US010393687B1

(12) United States Patent
Ostashev

(10) Patent No.: US 10,393,687 B1
(45) Date of Patent: Aug. 27, 2019

(54) MULTI-DIRECTIONAL WATER SENSOR

(71) Applicant: Glentronics, Inc., Lincolnshire, IL (US)

(72) Inventor: Ilya Ostashev, Lincolnshire, IL (US)

(73) Assignee: Glentronics, Inc., Lincolnshire, IL (US)

( * ) Notice: Subject to any disclaimer, the term of this patent is extended or adjusted under 35 U.S.C. 154(b) by 3 days.

(21) Appl. No.: 16/036,602

(22) Filed: Jul. 16, 2018

(51) Int. Cl.
*G08B 21/20* (2006.01)
*G01N 27/07* (2006.01)

(52) U.S. Cl.
CPC ............. *G01N 27/07* (2013.01); *G08B 21/20* (2013.01)

(58) Field of Classification Search
CPC .................................. G01N 27/07; G08B 21/20
USPC ........................................................ 324/693
See application file for complete search history.

(56) References Cited

U.S. PATENT DOCUMENTS

| 4,227,190 | A |  | 10/1980 | Kelley |  |
|---|---|---|---|---|---|
| 4,264,902 | A |  | 4/1981 | Miller |  |
| 4,845,472 | A |  | 7/1989 | Gordon |  |
| 5,091,715 | A |  | 2/1992 | Murphy |  |
| 5,272,467 | A |  | 12/1993 | Krauleidies |  |
| 5,757,197 | A | * | 5/1998 | O'Neill | .............. G01F 23/24 324/446 |
| 6,690,281 | B2 |  | 2/2004 | Palmer |  |
| 8,970,385 | B1 |  | 3/2015 | Brooking |  |
| 8,970,386 | B2 |  | 3/2015 | Scharf |  |
| 2013/0069675 | A1 | * | 3/2013 | Woloszyk | ............. G01R 27/22 324/693 |

* cited by examiner

*Primary Examiner* — Reena Aurora
(74) *Attorney, Agent, or Firm* — Nixon Peabody LLP

(57) ABSTRACT

A multi-directional water sensor comprises a housing having multiple conductive pads on the outer surface of the housing at locations spaced around the periphery of the housing, an electrical power source coupled to the conductive pads, and multiple electrical conductors located inside the housing and connecting multiple pairs of the contacts so that electrical current can flow between different pairs of the contacts when they are connected by water. The housing may have a generally rectangular shape, with the contacts located at the corners of the housing. The multiple electrical conductors are connected to an alarm that is energized when electrical current flows between any pair of the contacts.

10 Claims, 7 Drawing Sheets

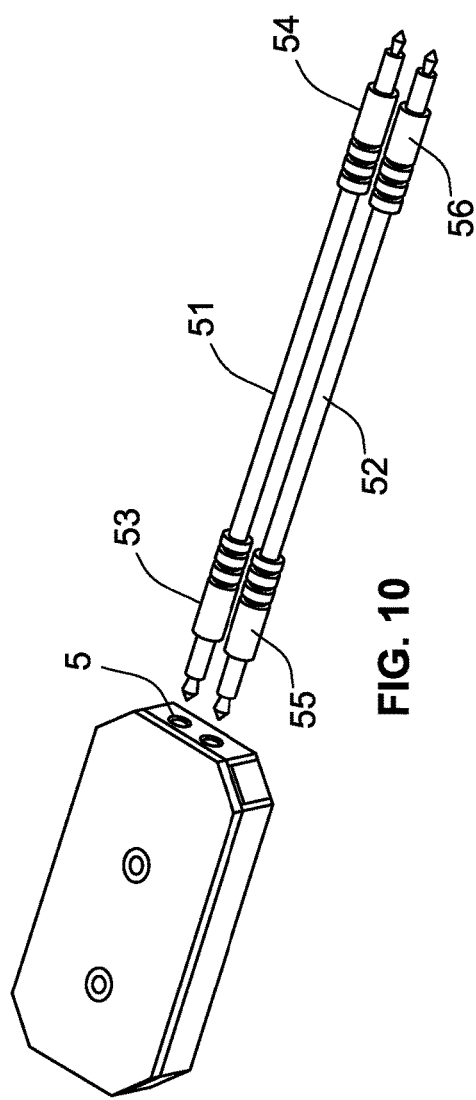
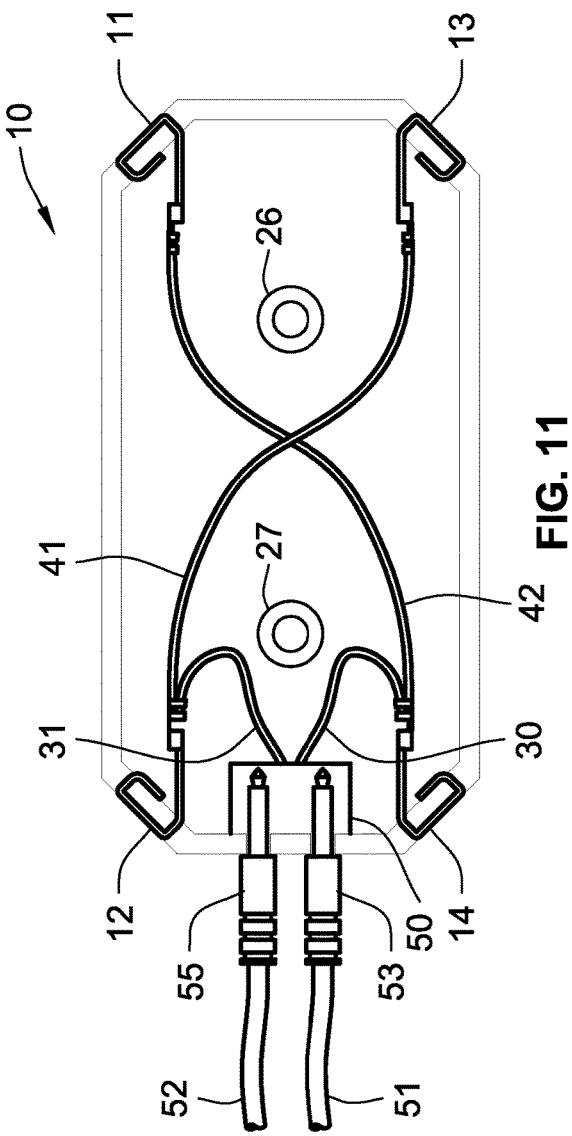
FIG. 10
FIG. 11

MULTI-DIRECTIONAL WATER SENSOR

FIELD OF THE INVENTION

The present invention relates generally to a multi-directional water sensor that detects water from any direction so that water can be reliably detected regardless of the orientation of the sensor. This enables the sensor to be located in a wide variety of different spaces of different sizes and shapes.

BACKGROUND

Water sensors or sensors are used to detect water leaks by sensing the presence of water in contact with two spaced conductive pads. If water comes into contact with both conductive pads, an audible alarm is sounded to warn the user that water is present in the location of the sensor. Such water sensors are typically placed under sinks or in areas where major appliances are located, such as in a laundry room.

BRIEF SUMMARY

In accordance with one embodiment, a multi-directional water sensor comprises a housing having multiple electrically conductive pads on the outer surface of the housing at locations spaced around the periphery of the housing, an electrical power source coupled to the conductive pads, and multiple electrical conductors located inside the housing and connecting multiple pairs of the conductive pads so that electrical current can flow between different pairs of the pads when they are connected by water.

In one embodiment, the water sensor housing has a generally rectangular shape, and the conductive pads are located at the corners of the housing. The multiple electrical conductors are connected to an alarm that is energized when electrical current flows between any pair of the conductive pads. The housing is preferably waterproof.

BRIEF DESCRIPTION OF THE DRAWINGS

FIG. 10 is a perspective view of a modified water sensor having one end adapted to receive a pair of plug-in cables.

FIG. 11 is a cross-section of the modified water sensor shown in FIG. 10.

DETAILED DESCRIPTION

Figure 1:
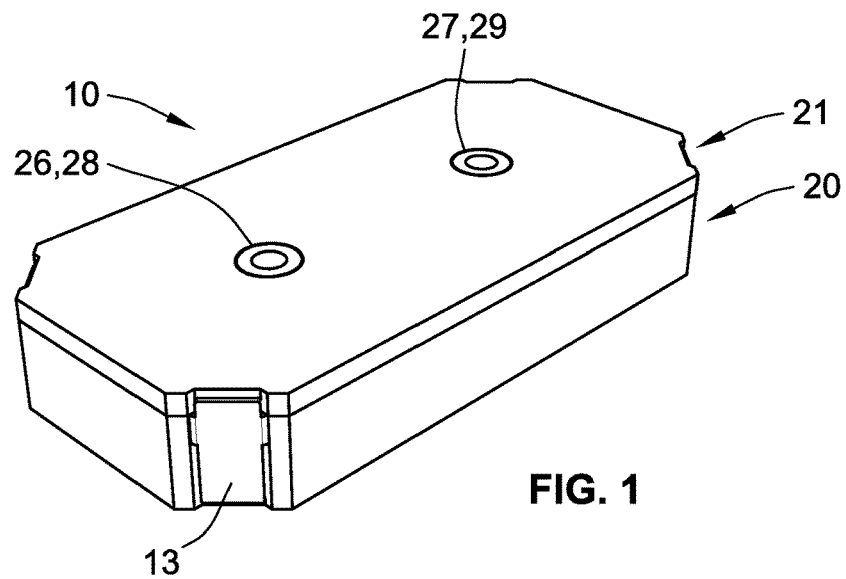
FIG. 1 is a top perspective view from one corner of a water sensor embodying the invention.
Figure 2:
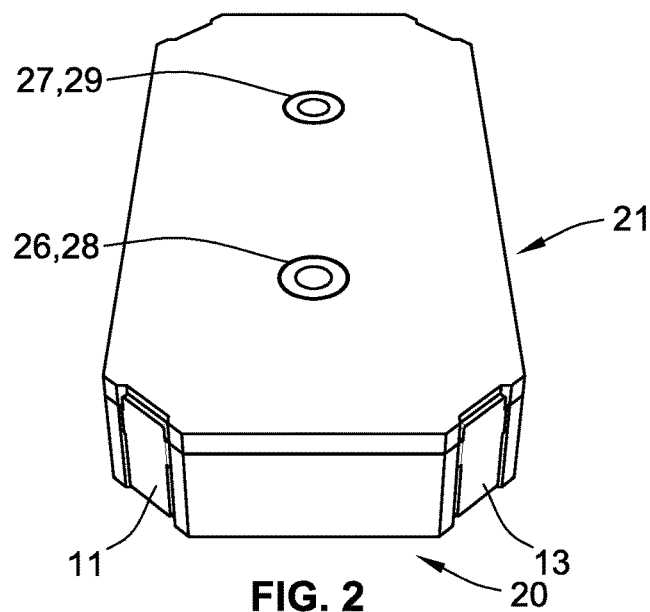
FIG. 2 is a top perspective view from one end of the water sensor shown in FIG. 1.
Figure 3:
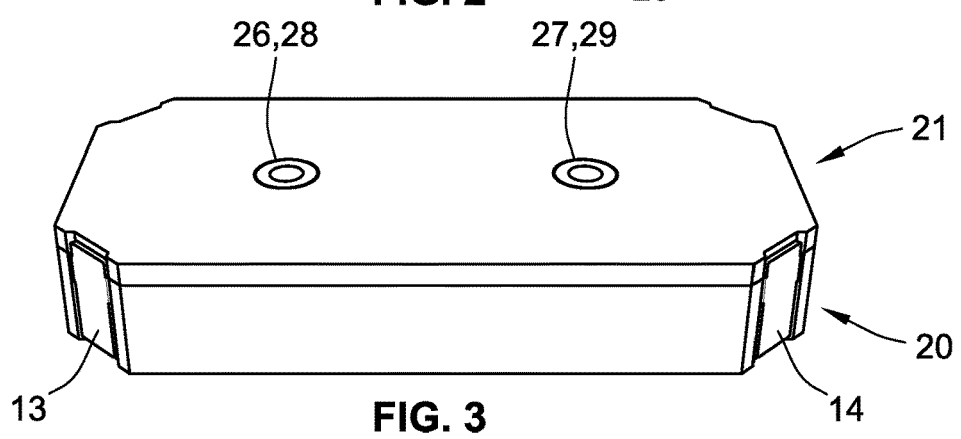
FIG. 3 is a top perspective view from one side of the water sensor shown in FIG. 1.

In the drawings, FIGS. 1-5 illustrate a multi-directional water sensor that has a rectangular housing 10 with four truncated corners, each of which includes one of four electrically conductive pads 11-14. The main body portion of the housing 10 is made of a non-conductive material, such as a molded polymeric material. An electrical cable 15 connects circuitry inside the housing 10 to an alarm device that produces an alarm sound and/or signal when water contacts any two of the conductive pads 11-14 and thus completes an electrical circuit. One example of a suitable alarm device is the "Pro Series Water Alarm" available from Glentronics Inc.

In the illustrative embodiment, the housing 10 includes a base member 20 and a lid 21 that has a peripheral depending flange 23 that fits flush against the top surface 24 of the peripheral side walls of the base member 20, as shown in FIGS. 1-3 and 5. The lid 21 includes a pair of integral pins 25a and 25b that depend from the bottom surface of the lid 21 and engage the bottom wall of the base member 20 when the housing 10 is assembled. The base member 20 includes a pair of integral posts 26 and 27 that fit into apertures 28 and 29 in the lid 21 when the base member 20 and lid 21 are assembled.

Figure 4A:
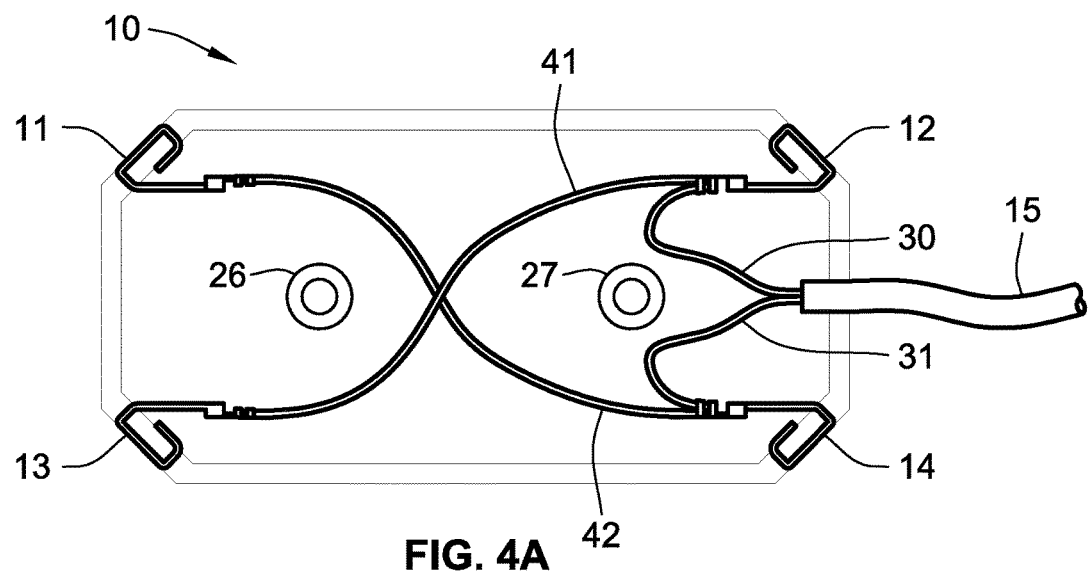
FIG. 4A is a top plan view of the water sensor shown in FIG. 1 with the lid removed.
Figure 4B:
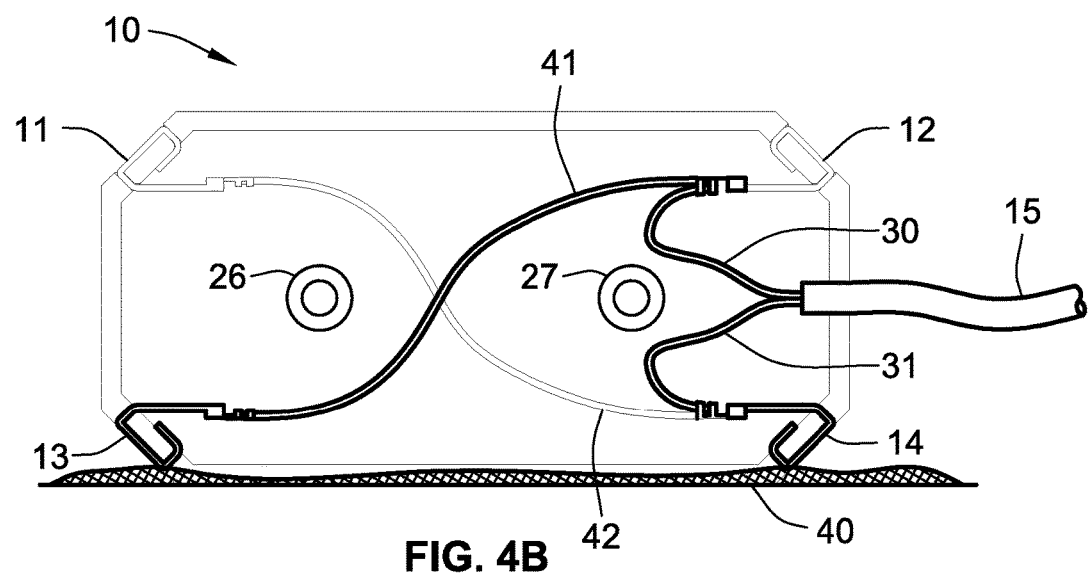
FIG. 4B is the same top plan view shown in FIG. 4A with water contacting one side of the water sensor.

FIGS. 4A and 4B are cross-sections of the water detector 10 shown in FIG. 1, showing the electrical circuitry inside the housing 10 for connecting the conductive pads 11-14 to the cable 15. Each of the conductive pads 11-14 extends diagonally across a corner of the housing 10, at an angle of 135 degrees to the adjacent side walls of the housing. As can be seen in FIGS. 4A and 4B, this angular orientation of the conductive pads 11-14 ensures that a conductive pad will be contacted by water passing along a housing side wall on either side of one of the pads 11-14. For example, in FIG. 4B water 40 is passing along the housing sidewall extending between the pads 13 and 14 of the housing 10. Both conductive pads 13 and 14 are contacted by the water 40, so electrical current can flow between pads 13 and 14. This causes current to flow from the cable 15 through conductors 30 and 41 to the pad 13, and then through the water 40 from pad 13 to pad 14. This current continues through the cable 15 to the alarm device, which produces an alert signal indicating that water is present in the location of the housing 10, so that remedial action can be taken. Only a small amount of electrical current, e.g., 2.2 µA, is needed to activate the alarm device.

It can be seen from FIGS. 4A and 4B that any given pair of conductive pads located at opposite ends of any of the four side walls of the housing 10 will be electrically connected to both wires of the cable 15 if water is present to connect that pair of pads.

Figure 5:
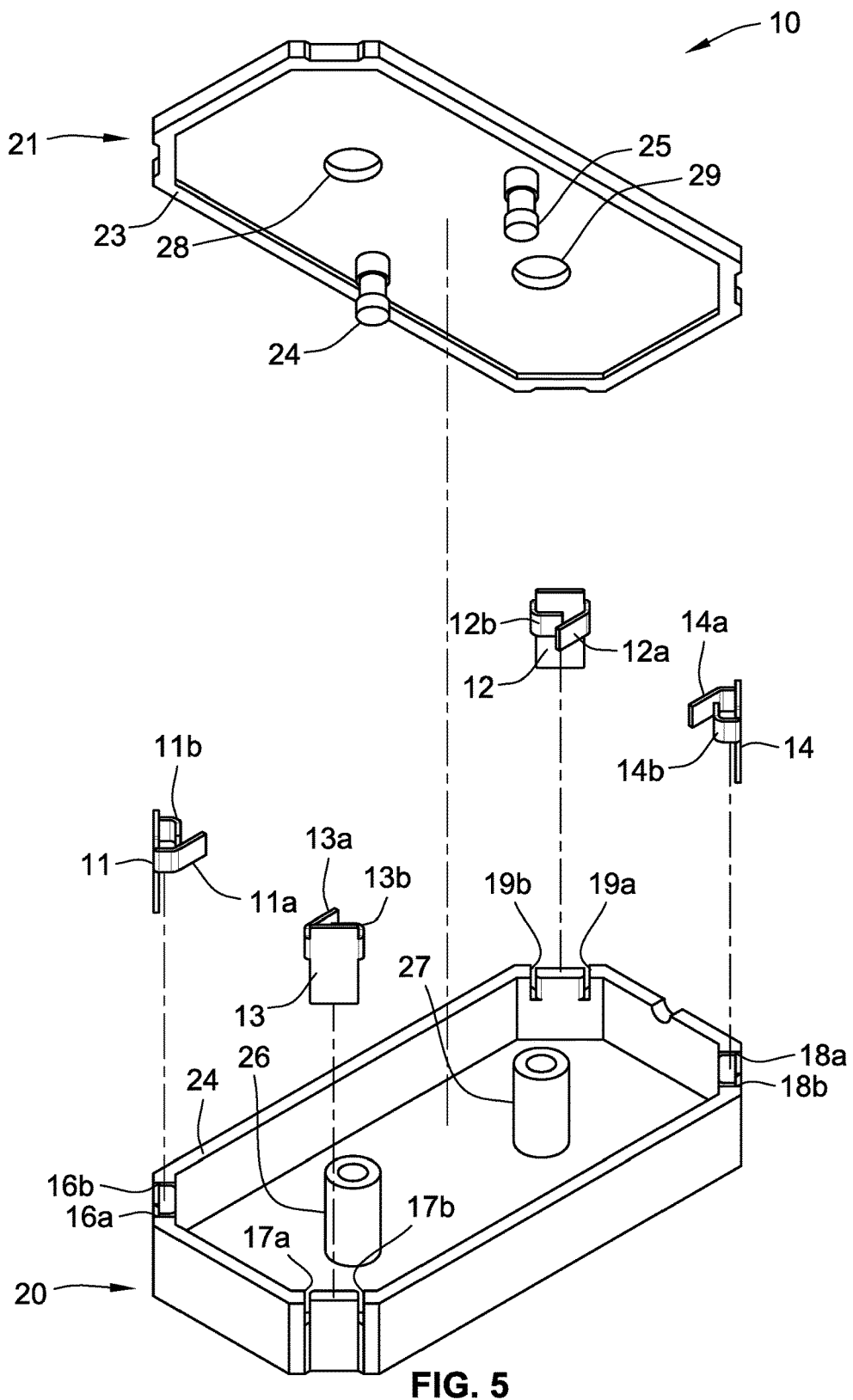
FIG. 5A is a top plan view of the water sensor of FIG. 1, with the cover plate removed.
FIG. 5B is a top plan view of FIG. 4A with water in contact with two of the conductive corner pads.

FIG. 5 illustrates one preferred structure of the conductive pads 11-14 to facilitate attaching the pads to the corners of the housing 10. Each of the pads 11-14 includes a pair of tabs 11a, 11b or 12a, 12b or 13a, 13b or 14a, 14b extending laterally from opposite side edges of the tabs. The projecting tabs of each pad fit into matching slots 16a, 16b or 17a, 17b or 18a, 18b or 19a, 19b in the truncated corners of the housing 10. The tabs 11b-14b are bent tightly around the respective truncated corners of the housing 10 to clamp the pads 11-14 tightly in place on the housing 10. Tabs 11a-14a are longer than tabs 11b-14b and are bent at only a 45-degree angle to facilitate connecting these tabs to the wires 30, 31, 41 and 42, which may be connected by soldering or by the use of conventional connectors such as "Faston" connectors.

Figure 6A:
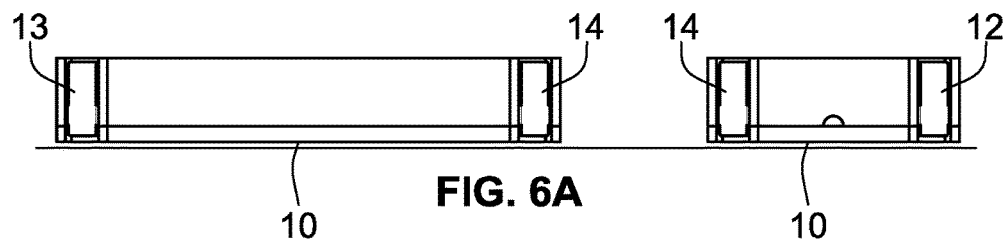
FIG. 6A is a pair of side and end elevations of the water sensor of FIG. 1
Figure 6B:
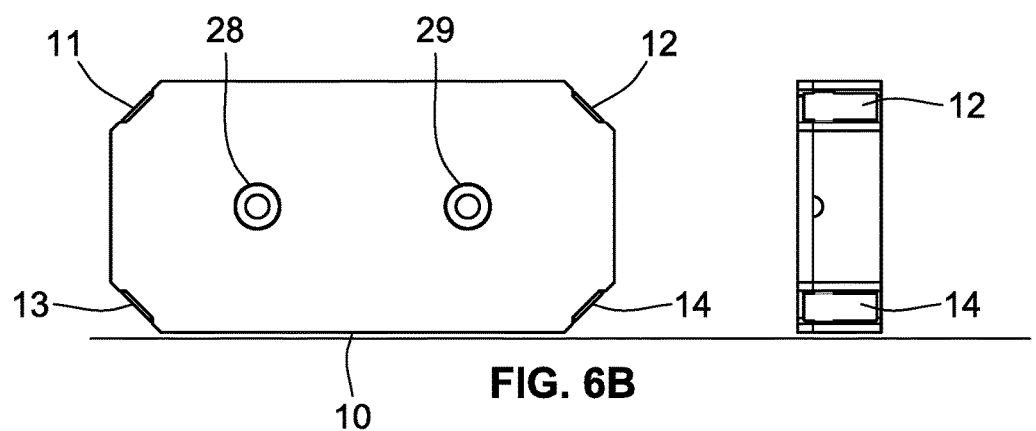
FIG. 6B is a pair of top and end elevations of the water sensor of FIG. 1, with the cover plate removed.
Figure 6C:
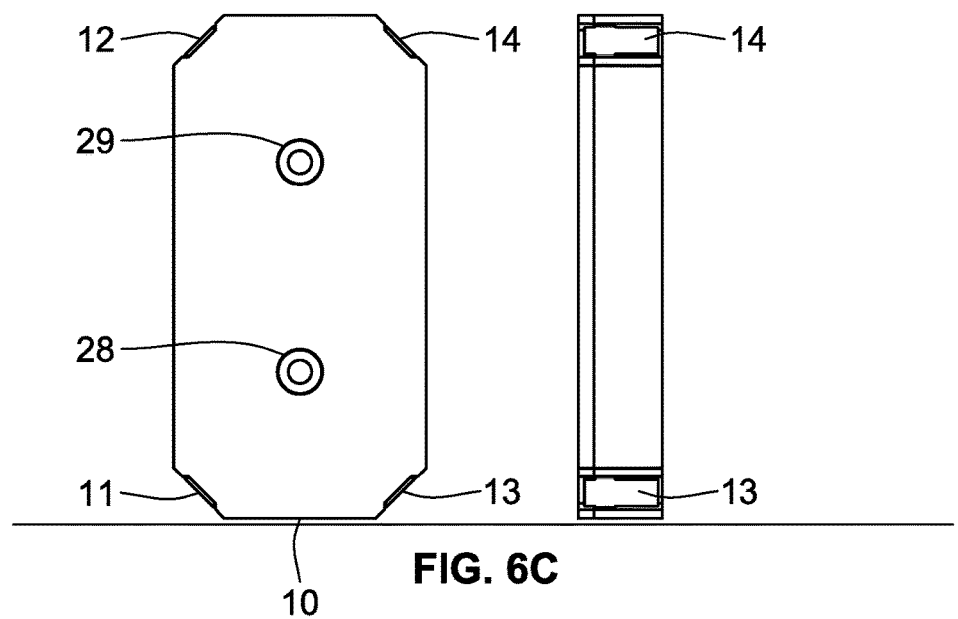
FIG. 6C is a pair of side and end elevations of the water sensor of FIG. 1.
Figure 7:
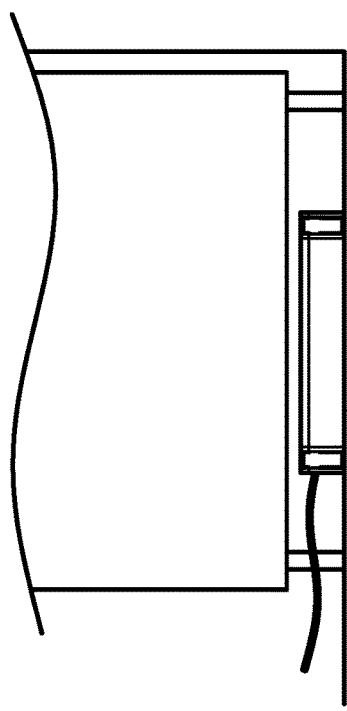
FIG. 7 is a fragmentary elevation of an appliance having the water sensor of FIG. 1 located beneath the bottom wall of the appliance.
Figure 8:
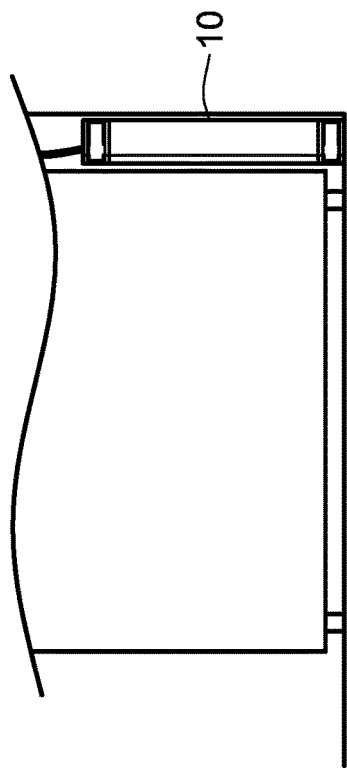
FIG. 8 is a fragmentary elevation of an appliance having the water sensor of FIG. 1 located adjacent the rear wall of the appliance.
Figure 9:
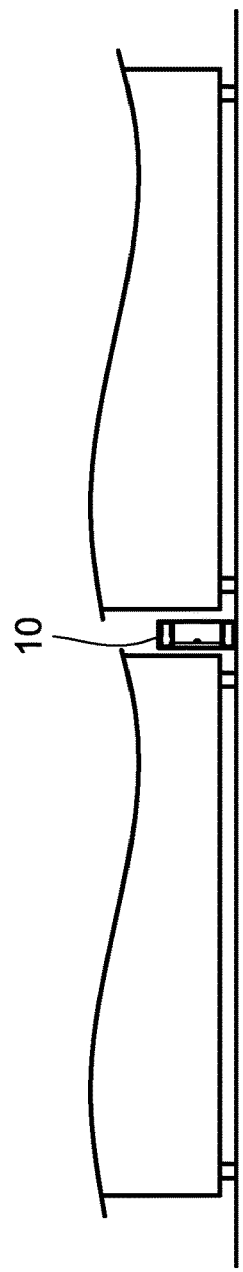
FIG. 9 is a fragmentary elevation of an appliance having the water sensor of FIG. 1 located between the side walls of two adjacent appliances.

The angled corner arrangement of the pads 11-14 permits the housing 10 to be positioned in a variety of different orientations on a surface where the presence of water is to be detected, as illustrated in FIGS. 6A-6C. The pads 11-14 can be located a predetermined distance above the floor when the housing 10 is resting on the floor, to allow moisture or a very thin layer of water to be present on the floor without triggering an electrical connection between the sensors. For example, the predetermined distance can be 1/32". In FIG. 6A the housing 10 rests on its bottom wall 30, in FIG. 6B the housing 10 rests on a side wall 31, and in FIG. 6C the housing 10 rests on an end wall 32. These different options enable the housing 10 to be positioned in a wide variety of different locations, such as beneath a major appliance as illustrated in FIG. 7, between an appliance and a wall as illustrated in FIG. 8, or between a pair of closely spaced appliances as illustrated in FIG. 9. In each of these applications, a pair of the conductive corner tabs 11-14 is located at opposite ends of the bottom surface of the housing 10 where water is to be detected.

To exclude moisture and corrosive agents, the housing 10 is preferably filled with a potting compound after the housing and its internal parts (described below) have been assembled. Conventional potting compounds, such as thermosetting plastics or silicone rubber, gels may be used.

Figure 12:
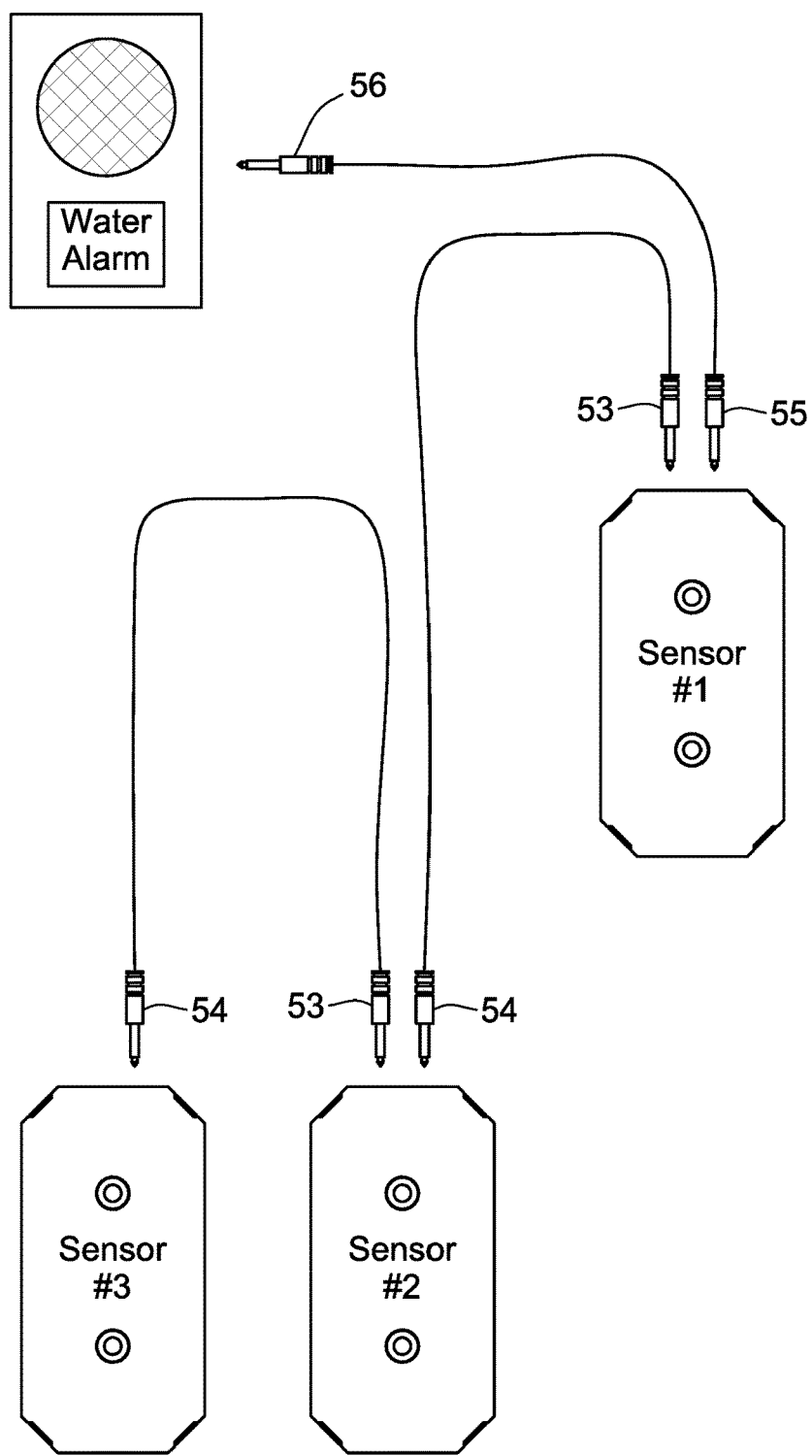
FIG. 12 is a schematic diagram of a single water alarm coupled to a chain of water sensors of the type illustrated in FIGS. 10 and 11.

FIGS. 10-12 illustrate a modified arrangement for replacing the cable 15 on the sensor with a dual female socket 40, such as a dual 3.5 mm female socket. Alternately, instead of a dual female socket, one or more individual female sockets can be present. The socket 40 receives a pair of cables 41a and 41b, each of which has a pair of 3.5-mm male jacks 53, 54 or 55, 56 at opposite ends for connecting that cable to corresponding 3.5-millimeter female sockets. For example, FIG. 12 illustrates one cable used to connect the sensor to a compatible device such as the water alarm described above, while the other cable is used to connect the sensor to one or more additional sensors in a chain. When any of the sensors comes into contact with water, the connected water alarm will sound an alarm. This allows the use of a single water alarm to be used with multiple sensors, e.g., for cost reduction.

While particular embodiments and applications of the present invention have been illustrated and described, it is to be understood that the invention is not limited to the precise construction and compositions disclosed herein and that various modifications, changes, and variations can be apparent from the foregoing descriptions without departing from the spirit and scope of the invention as defined in the appended claims.

The invention claimed is:

1. A multi-directional water sensor comprising
 a housing having multiple conductive pads on the outer surface of the housing, each of the conductive pads extending diagonally across respective corners of the housing, wherein the multiple conductive pads include at least two distinct pairs of the conductive pads spaced around the periphery of the housing such that electrical current can flow between one of the at least two distinct pairs of conductive pads responsive to being electrically connected by a very thin layer of surface water responsive to the housing resting on at least two different walls of the housing in at least two different orientations, wherein the at least two different walls include at least two of a side wall, an end wall, a bottom wall, or a top wall,
 an electrical power source coupled to said conductive pads, and
 multiple electrical conductors located inside said housing and connecting the at least two distinct pairs of said conductive pads, the at least two distinct pairs of conductive pads including (a) a first pair having a first conductive pad and a second conductive pad electrically connected by a first of the multiple electrical conductors and (b) a second pair having a third conductive pad and one of the first conductive pad or the second conductive pad electrically connected by a second of the multiple electrical conductors.

2. The water sensor of claim 1 in which said housing has a generally rectangular shape, the very thin layer of surface water having a minimum height of 1/32" above an exterior surface upon which the housing rests.

3. The water sensor of claim 1 in which said multiple electrical conductors are connected to an alarm that is energized when electrical current flows between different ones of the at least two distinct pairs of conductive pads.

4. The water sensor of claim 1 in which said housing is waterproof.

5. The water sensor of claim 1 in which said multiple electrical conductors are connected to multiple sockets so that multiple cables can be coupled to said sockets so that said conductors can be coupled to both an alarm and at least one additional water sensor.

6. A method of sensing water comprising
 placing a housing having multiple conductive pads on an exterior surface where water is to be detected, said pads including at least two distinct pairs of conductive pads on the outer surface of the housing spaced around the periphery of the housing such that electrical current can flow between one of the at least two distinct pairs of conductive pads when they are connected by water on a surface upon which the housing rests responsive to the housing resting on at least two different walls of the housing in at least two different orientations, each of the pads extending diagonally across respective corners of the housing, wherein the at least two different walls include at least two of a side wall, an end wall, a bottom wall, or a top wall, and
 coupling an electrical power source to the at least two distinct pairs of said conductive pads, the at least two distinct pairs including a first pair having a first conductive pad and a second conductive pad and a second pair having a third conductive pad and one of the first conductive paid or the second conductive pad, the coupling including electrically connecting a first of multiple electrical conductors located inside said housing between the first pair and electrically connecting a second of the multiple electrical conductors between the second pair.

7. The method of claim 6 in which said housing has a generally rectangular shape.

8. The method of claim 6 which includes energizing an alarm when electrical current flows between different pairs of said conductive pads.

9. The method of claim 6 in which said housing is waterproof.

10. The method of claim 6 which includes coupling said multiple electrical conductors to both an alarm and at least one additional water sensor.

* * * * *